United States Patent [19]

Boutonnat et al.

[11] Patent Number: 4,475,378
[45] Date of Patent: Oct. 9, 1984

[54] PROCESS FOR INTERROGATION OF A DETECTOR OF THE CONCENTRATION OF COMBUSTIBLE GAS AND AN IMPLEMENTING DEVICE

[75] Inventors: Maurice Boutonnat, Gouvieux; Gerard Rose, Villers Saint Paul, both of France

[73] Assignee: CdF Chimie S.A., Bully-les-Mines, France

[21] Appl. No.: 443,108

[22] Filed: Nov. 19, 1982

[30] Foreign Application Priority Data

Nov. 20, 1981 [FR] France .................. 81 21733

[51] Int. Cl.³ .................................. G01N 27/12
[52] U.S. Cl. .............................. 73/23; 340/634
[58] Field of Search ............ 73/23, 27 R; 340/633, 340/634; 422/94, 96, 98

[56] References Cited

U.S. PATENT DOCUMENTS

| | | | |
|---|---|---|---|
| 3,678,489 | 7/1972 | Scherban | 340/633 X |
| 3,932,807 | 1/1976 | Wilson | 73/23 X |
| 4,020,480 | 4/1977 | Gotley | 340/633 X |
| 4,028,057 | 6/1977 | Nelson | 340/633 X |
| 4,031,747 | 6/1977 | Blanke | 73/23 X |
| 4,237,721 | 12/1980 | Dolan | 73/23 |
| 4,344,317 | 8/1982 | Hattori | 73/23 |
| 4,352,087 | 9/1982 | Wittmaier | 73/23 X |

FOREIGN PATENT DOCUMENTS 1397436 3/1964 France .
1155481 6/1969 United Kingdom .

Primary Examiner—Stephen A. Kreitman
Assistant Examiner—Vincent P. Kovalick
Attorney, Agent, or Firm—Finnegan, Henderson, Farabow, Garrett & Dunner

[57] ABSTRACT

A two stage process for interrogating a detector of the concentration of combustible gas in an atmosphere. In a first stage, the detector is supplied with a low voltage and the supply is cut and an optional alarm is sounded if a positive signal has been detected. In a second stage, if the signal detected in the first stage is negative or zero, then the detector is supplied with a second, higher voltage. The signal is compared to a predetermined range and, if not within that range, an optional alarm is sounded. A device to apply the process comprising a detector, an amplifier of the signal issued by the detector, a voltage reducing circuit, and a switch that controls the voltage reducing circuit slaved by a discriminator to the sign and/or to the maximum amplitude of the signal output by the amplifier. Application of the process and device to the detection of the concentration of methane.

12 Claims, 1 Drawing Figure

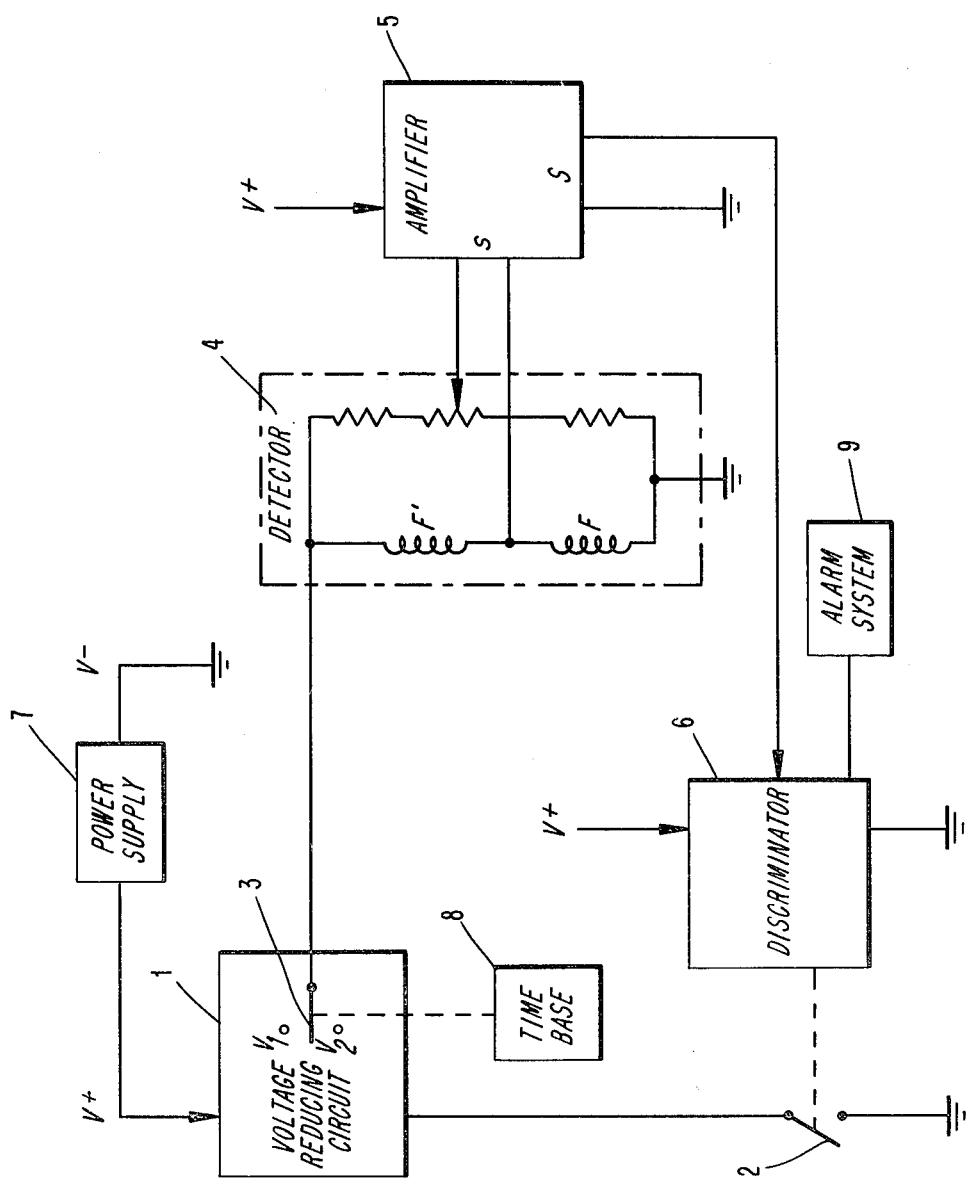

PROCESS FOR INTERROGATION OF A DETECTOR OF THE CONCENTRATION OF COMBUSTIBLE GAS AND AN IMPLEMENTING DEVICE

BACKGROUND OF THE INVENTION

The present invention relates to a new process for interrogation of a detector of the concentration of combustible gas and a device for its implementation. Different types of explosimeters are known that measure the concentration of combustible gas in an atmosphere by catalytic combustion on a platinum filament. The catalytic combustion heats the platinum wire and varies the resistance of the wire. This resistance change can unbalance a Wheatstone bridge fed from a source of direct current if the filament is placed in the bridge, and this imbalance can be measured. A metal filament coated with a porous refractory material is also known as a suitable filament for such a detector.

A discontinuous interrogation of the detector is the method generally used, especially for automatic explosimeters. For certain gases, in particular methane, the result of an interrogation of the detector in an atmosphere having a large concentration of gas is normally constituted by the inversion of the measurement signal issued by the detector. A specific treatment of the filament is generally necessary to obtain this inversion.

The difficulty with single voltage interrogation systems is that using the inversion of the signal issued by the detector does not totally guarantee the certainty of a large concentration of combustible gas in the atmosphere considered, especially for automatic detectors with discontinuous interrogation. More precisely, it has been established that the phenomenon of measurement signal inversion is not reproducible and that certain detectors, even in new condition, can give ambiguous indications of the combustible gas concentration.

SUMMARY OF THE INVENTION

An object of the present invention is to provide a reliable solution for the safety problem posed by measurement signal inversion.

An additional object of the present invention is to interrogate a detector of the concentration of combustible gas using a process that unambiguously indicates whether the concentration of a combustible gas in an atmosphere is or is not greater than a predetermined threshold concentration.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purposes of the invention, as embodied and broadly described herein, the invention comprises a process for interrogating a detector of the concentration of combustible gas supplying a polarized unbalancing signal comprising the steps of: applying a first voltage to the detector for a first time period of an interrogation sequence, wherein the first voltage is cut upon detection of a positive signal from the detector; applying a second voltage, higher than the first voltage, to the detector for a second time period, but only if the signal from the detector has been less than or equal to zero during the first time period; and measuring the signal produced by the detector when the second voltage is applied against a predetermined value.

The invention further comprises a device for detecting the concentration of a combustible gas in an atmosphere comprising: means for alternately producing a first voltage and a second voltage, wherein the first voltage is lower than the second voltage; means for detecting the concentration of the combustible gas in the atmosphere, wherein the detecting means is coupled with the producing means and emits a polarized unbalancing signal in response to the combustible gas and an applied voltage; means for comparing the polarized unbalancing signal with a predetermined minimum signal amplitude and a predetermined maximum signal amplitude; and means for stopping the first voltage from being further applied if the polarized unbalancing signal produced in response to the first voltage is not within a predetermined range and for stopping the second voltage from being applied to the detecting means if the polarized unbalancing signal produced in response to the first voltage is not within a predetermined range.

BRIEF DESCRIPTION OF THE DRAWINGS

While this specification concludes with claims particularly pointing out and distinctly claiming that which is regarded as the present invention, the objects and advantages of the device of the present invention may be more readily ascertained from the following description of the preferred embodiment when read in conjunction with the accompanying drawing.

The FIGURE is a schematic drawing of the device of the present invention.

DESCRIPTION OF THE PREFERRED EMBODIMENTS

Reference will now be made in detail to the presently preferred embodiments of the invention.

The process of the present invention comprises a two stage interrogation. In the first stage, from time 0 to time $t_1$ of the interrogation sequence, the detector is supplied with a first voltage, $V_1$, and the voltage is cut if a positive signal is detected. In the second stage, if the signal delivered by the detector has been negative or zero up to time $t_1$, then the detector is supplied, from time $t_1$ to time $t_2$ of the interrogation sequence, with a second voltage, $V_2$, higher than $V_1$. The maximum amplitude of the signal at time $t_2$ is measured and compared to a predetermined value.

If the signal becomes positive during the first stage of the process, oxidation has occurred, and there is a high amount of combustible gas present, thus it is unnecessary to proceed with the measurement using the filament needlessly. Yet, if the signal remains negative or zero during the first stage of the process, no conclusion may be reached, and a second voltage, $V_2$, greater than $V_1$, must be applied. If the signal measured in the second stage of the process is negative, inversion has occurred in the detector and the concentration of combustible gas is known to be high. If the signal measured at the end of the second stage of the process is positive, the concentration of combustible gas is low and may be measured against a predetermined maximum amplitude of a signal produced in the presence of a known concentration of combustible gas. The concentration of combustible gas, as measured by the signal amplitude, may trigger an alarm device.

Selection of the operating parameters for the process of the present invention, $t_1$, $t_2$, $V_1$, and $V_2$, depends on the combustible gas to be detected. The parameters may also be selected so that the total duration of the interrogation is not too large, and so that the process may be applied to detectors of any type and model without giving ambiguous indications.

A combustible gas, for purposes of the present invention, includes, but is not necessarily limited to, saturated hydrocarbons having from 1 to 4 carbon atoms and ethylene.

To optimize the parameters discussed above for methane, it is preferable to choose the following parameters when using conventional detectors: $t_1$ should be between 0.5 and 0.7 seconds, $t_2$ should be between 1.9 and 2 seconds, $V_1$ should be between 0.9 and 1.0 volt, and $V_2$ should be between 1.2 and 1.4 volts. Under these parameters, the time that the first voltage, $V_1$, is applied is 0.5 to 0.7 seconds, and the time that the second voltage, $V_2$, is applied, if necessary, is between 1.2 and 1.5 seconds.

Under these operating conditions, the process of the invention ensures a reliable determination of the concentration of a combustible gas in an atmosphere, whatever that concentration may be.

The process of the invention provides an additional benefit compared with a single interrogation process at a single voltage. In single interrogation processes, repeated measurement at high concentrations of combustible gas, for example amounts of methane greater than 30%, tended to modify the characteristic of the signal curve because cracking of the methane caused carbon deposits to form on the detector filament. Cutting the detector supply once a positive signal has been detected in the first stage of the process of the invention suppresses this parasitic carbon deposition.

The process of the invention is of very general application and does not depend on the nature of the filament. It is applicable to any measurement device supplying a polarized unbalancing signal of any amplitude, whether or not signal inversion is a factor in the measurements.

The process of the invention is especially beneficial in the detection of methane in coal mines.

The present invention also comprises a device for detecting the concentration of combustible gas in an atmosphere that implements the process described above.

The device comprises means for alternately producing a first voltage and a second voltage wherein the first voltage is lower than the second voltage. As embodied herein and illustrated by the attached drawing, though without implying a limitation, the voltage producing means includes a voltage reducing circuit 1, connected to the ground by switch 2 and connected to a detector 4 by a switch 3. This circuit supplies a first voltage, $V_1$, and a second voltage, $V_2$, higher than $V_1$, derived from a power supply device 7. A timebase 8, capable of initializing the interrogation sequence, acts on switch 3.

The device further comprises means for detecting the concentration of the combustible gas in the atmosphere. As embodied herein and illustrated by the attached drawing, though without implying a limitation, the detecting means includes a detector 4 that emits a polarized unbalancing signal. This detector may be a Wheatstone bridge. An amplifier 5 may be included in the detecting means to boost the polarized unbalancing signal received from the detector.

The device further comprises means for comparing the polarized unbalancing signal with a predetermined minimum signal amplitude and a predetermined maximum signal amplitude for the signal produced in response to the first voltage and for the signal produced in response to the second voltage. As embodied herein and illustrated by the attached drawing, though without implying a limitation, the comparing means includes a discriminator 6 comprising known circuits that carry out logic operations.

The device further comprises means for stopping the first voltage from being further applied if the signal produced in response to the first voltage is not within a predetermined range and for stopping the second voltage from being applied to the detecting means if the polarized unbalancing signal produced in response to the first voltage is not within a predetermined range. As embodied herein and illustrated by the attached drawing, though without implying a limitation, the stopping means includes a switch 2 slaved to the discriminator 6 that is closed or opened in response to the action of the discriminator 6 after it evaluates the signal emitted from either the detector 4 or the amplifier 5.

The detector 4 may be a Wheatstone bridge whose four arms are formed respectively by a filament detector F, a filament compensator F', a resistor, and a resistor in series with a potentiometer for adjusting the zero. Zero is established by adjustment carried out in the absence of any trace of combustible gas. During detection of the presence of combustible gas in an atmosphere, the bridge is subjected to the interrogation signal and generates a signal of imbalance, s, which is generally a voltage.

The amplifier 5 may be a direct current amplifier with a power supply provided by a positive voltage source. The amplifier 5 transforms the value of the signal, s, to a higher value, S.

The voltage adjustment circuit 1 includes elements capable of reducing voltage supplied by the positive source to two chosen values $V_1$ and $V_2$, $V_1$ being less than $V_2$. The source of positive voltage may be one or more dry cells, a battery, or a transformer-rectifier fed from mains and preferably including a stabilizer circuit. Switches 2 and 3 may be of any known type. They are advantageously of the electronic type.

The discriminator 6 is composed of circuits carrying out logic operations; it slaves the switch 2 to the sign and/or to the maximum amplitude of the signal S. The timebase 8 that initializes the interrogation sequence is controlled either manually or electronically.

The device of the invention may advantageously be associated with an alarm system 9 controlled by the sign and/or the maximum amplitude of the signal, S or s, and connected either to the amplifier 5 or, as shown on the attached FIGURE, to the discriminator 6. The alarm may be audible and/or visual. The device of the invention may also be associated with a system for processing the signal, S or s, connected to the amplifier 5 and capable of converting the maximum amplitude of the polarized unbalancing signal into a reading showing the concentration of combustible gas.

The device of the invention operates as follows. At time $t=0$ the initialization of the interrogation sequence causes switches 2 and 3, previously open, to close. Switch 3 closes at position $V_1$. At time $t_1$, if the signal, S, is positive, the discriminator 6 causes the switch 2 to open, and the associated alarm signal is triggered. At time $t_1$, if the signal S is negative or zero, the discriminator keeps the switch 2 closed and the time-base 8 toggles the switch 3 to the position $V_2$, thus triggering the second phase of the interrogation sequence. At time $t_2$, the end of the interrogation sequence, if the signal S remains negative or zero, the associated alarm system is triggered; if the signal is positive, then the associated alarm system will only be triggered if the value of the signal S is greater than a predetermined threshold amplitude for an undesirable concentration of combustible gas. At time $t_2$, the discriminator 6 opens the switch 2 and the timebase 8 opens the switch 3. In every operating case described above, the system for processing the signal S associated with the device according to the invention makes it possible to know the concentration of combustible gas detected.

It will be obvious to those skilled in the art that various modifications and variations could be made in the invention without departing from its scope.

What is claimed is:

1. A process for interrogating a detector of the concentration of combustible gas supplying a polarized unbalancing signal comprising the steps of:
   (a) applying a first voltage to said detector for a first time period of an interrogation sequence, wherein said first voltage is cut upon detection of a positive signal from said detector;
   (b) applying a second voltage, higher than said first voltage, to said detector for a second time period, but only if the signal from said detector has been less than or equal to zero during said first time period; and
   (c) measuring the signal produced by said detector when said second voltage is applied against a predetermined maximum value and a predetermined minimum value.

2. The process of claim 1, wherein said first time period is between 0.5 and 0.7 seconds, said second time period is between 1.2 and 1.5 seconds, said first voltage is between 0.9 and 1.0 volts and said second voltage is between 1.2 and 1.4 volts.

3. The process of claim 1, wherein said combustible gas is methane.

4. A device for detecting the concentration of a combustible gas in an atmosphere comprising:
   (a) means for alternately producing a first voltage and a second voltage, wherein said first voltage is lower than said second voltage;
   (b) means for detecting the concentration of said combustible gas in said atmosphere, wherein said detecting means is coupled with said producing means and emits a polarized unbalancing signal in response to said combustible gas and an applied voltage;
   (c) means for comparing said polarized unbalancing signal with a predetermined minimum signal amplitude and a predetermined maximum signal amplitude; and
   (d) means for stopping said first voltage from being further applied if said polarized unbalancing signal produced in response to said first voltage is not within a predetermined range and for stopping said second voltage from being applied to said detecting means if said polarized unbalancing signal produced in response to said first voltage is not within a predetermined range.

5. A device for detecting the concentration of a combustible gas in an atmosphere comprising:
   (a) a voltage reducing circuit capable of producing a first voltage and a second voltage, higher than said first voltage;
   (b) a power source coupled with said voltage reducing circuit;
   (c) timing means for first applying said first voltage for a first time period and then applying said second voltage for a second time period;
   (d) a detector coupled with said voltage reducing circuit that produces a polarized unbalancing signal in response to said voltage reducing circuit and the presence of said combustible gas;
   (e) an amplifier coupled with said detector that amplifies said polarized unbalancing signal;
   (f) a discriminator coupled with said amplifier that compares said amplified polarized unbalancing signal to a predetermined maximum and minimum; and
   (g) means for controlling said voltage reducing circuit coupled with said voltage reducing circuit and coupled with said discriminator, wherein said controlling means prevents said first voltage from being applied for the entirety of said first time period if said polarized unbalancing signal produced in response to said voltage reducing circuit and said combustible gas during said first time period is not within a predetermined range and wherein said controlling means further prevents said second voltage from being applied to said detector if said polarized unbalancing signal produced in response to said voltage reducing circuit and said combustible gas during said first time period is not within a predetermined range.

6. The device of claim 5, wherein said device further comprises an alarm connected to said amplifier and controlled by the sign of said polarized unbalancing signal, the maximum amplitude of said polarized unbalancing signal, or some combination thereof.

7. The device of claim 5, wherein said device further comprises an alarm system connected to said discriminator and controlled by the sign of said polarized unbalancing signal, the maximum amplitude of said polarized unbalancing signal, or some combination thereof.

8. The device of claim 5, wherein said device further comprises means for processing an amplified polarized unbalancing signal, coupled to said amplifier and capable of converting the maximum amplitude of said polarized unbalancing signal to the concentration of combustible gas.

9. The device of claim 8, wherein said device further comprises means for displaying said concentration of said combustible gas coupled with said processing means.

10. The device of claim 5, wherein said timing means applies said first voltage for 0.5 to 0.7 seconds and then applies said second voltage for 1.2 to 1.5 seconds.

11. The device of claim 5, wherein said first voltage is between 0.9 and 1.0 volts and said second voltage is between 1.2 and 1.4 volts.

12. The device of claim 10, wherein said first voltage is between 0.9 and 1.0 volts and said second voltage is between 1.2 and 1.4 volts.

* * * * *